United States Patent
Klein et al.

(10) Patent No.: US 9,067,865 B2
(45) Date of Patent: Jun. 30, 2015

(54) ETHERAMINES AND THEIR USE AS INTERMEDIATES FOR POLYMER SYNTHESIS

(75) Inventors: Howard P. Klein, Austin, TX (US); Terry L. Renken, Conroe, TX (US); Martin J. Renner, Hallettsville, TX (US); Bruce L. Burton, Spring, TX (US); Katty Darragas, Oudenaarde (BE)

(73) Assignee: HUNTSMAN PETROCHEMICAL LLC, The Woodlands, TX (US)

( * ) Notice: Subject to any disclaimer, the term of this patent is extended or adjusted under 35 U.S.C. 154(b) by 0 days.

(21) Appl. No.: 13/516,879

(22) PCT Filed: Dec. 21, 2010

(86) PCT No.: PCT/US2010/061591
§ 371 (c)(1),
(2), (4) Date: Jun. 18, 2012

(87) PCT Pub. No.: WO2011/087793
PCT Pub. Date: Jul. 21, 2011

(65) Prior Publication Data
US 2012/0259075 A1 Oct. 11, 2012

Related U.S. Application Data

(60) Provisional application No. 61/289,155, filed on Dec. 22, 2009.

(51) Int. Cl.
| | | |
|---|---|---|
| C07C 217/42 | (2006.01) | |
| C07C 213/02 | (2006.01) | |
| C08G 59/50 | (2006.01) | |
| C08G 59/56 | (2006.01) | |
| C08G 18/08 | (2006.01) | |
| C08G 18/32 | (2006.01) | |

(52) U.S. Cl.
CPC .......... *C07C 217/42* (2013.01); *C08G 59/5006* (2013.01); *C08G 59/56* (2013.01); *C08G 18/08* (2013.01); *C08G 18/32* (2013.01); *C07C 213/02* (2013.01)

(58) Field of Classification Search
CPC ............................. C07C 217/42; C07C 213/02
See application file for complete search history.

(56) References Cited

U.S. PATENT DOCUMENTS

| | | | |
|---|---|---|---|
| 2,683,730 A | 7/1954 | Seeger et al. | |
| 2,950,263 A | 8/1960 | Abbotson et al. | |
| 3,012,008 A | 12/1961 | Lister | |
| 3,152,998 A | 10/1964 | Moss | |
| 3,344,162 A | 9/1967 | Rowton | |
| 3,362,979 A | 1/1968 | Bentley | |
| 3,394,164 A | 7/1968 | McClellan et al. | |
| 3,654,370 A * | 4/1972 | Yeakey | 564/480 |
| 3,847,992 A * | 11/1974 | Moss | 564/479 |
| 4,014,933 A | 3/1977 | Boettger et al. | |
| 4,152,353 A | 5/1979 | Habermann | |
| 4,436,891 A * | 3/1984 | Umeda et al. | 528/111 |
| 4,588,840 A * | 5/1986 | Gurgiolo | 564/443 |
| 4,705,814 A | 11/1987 | Grigsby, Jr. et al. | |
| 4,748,192 A | 5/1988 | Smith | |
| 4,766,245 A | 8/1988 | Larkin et al. | |
| 4,769,438 A * | 9/1988 | Zimmerman et al. | 528/104 |
| 5,235,007 A * | 8/1993 | Alexander et al. | 525/523 |
| 5,502,151 A | 3/1996 | Wantanabe | |
| 5,567,748 A | 10/1996 | Klein et al. | |
| 5,639,413 A | 6/1997 | Crivello | |
| 5,696,293 A * | 12/1997 | Phillips et al. | 564/480 |
| 5,958,825 A * | 9/1999 | Wulff-Doring et al. | 502/300 |
| 5,972,563 A | 10/1999 | Steinmann et al. | |
| 6,245,835 B1 * | 6/2001 | Klein et al. | 523/402 |
| 7,078,475 B2 * | 7/2006 | Klein et al. | 528/64 |
| 7,550,550 B2 | 6/2009 | Klein et al. | |
| 2006/0160980 A1 * | 7/2006 | Klein et al. | 528/44 |
| 2007/0208156 A1 * | 9/2007 | Posey et al. | 528/44 |
| 2007/0208157 A1 * | 9/2007 | Posey et al. | 528/44 |
| 2007/0292620 A1 * | 12/2007 | Volle et al. | 427/386 |

FOREIGN PATENT DOCUMENTS

| | | | |
|---|---|---|---|
| BE | 677124 A | * | 3/1966 |
| JP | 49-32680 | | 9/1974 |
| JP | 49032680 | * | 9/1974 |
| WO | 2004020506 | | 3/2004 |

* cited by examiner

*Primary Examiner* — Randy Gulakowski
*Assistant Examiner* — Ha Nguyen
(74) *Attorney, Agent, or Firm* — Huntsman International LLC

(57) ABSTRACT

The present invention relates to an etheramine mixture containing a monoether diamine and its method of production by alkoxylating an initiator with an alkylene oxide to produce a precursor polyol and reductively aminating the precursor polyol to form the etheramine mixture. The etheramine mixture may be used in variety of applications including as a curing agent for an epoxy resin or as a reactant in the production of polyurea.

20 Claims, No Drawings

ETHERAMINES AND THEIR USE AS INTERMEDIATES FOR POLYMER SYNTHESIS

CROSS-REFERENCE TO RELATED APPLICATIONS

This application is the National Phase of International Application PCT/US2010/061591 filed Dec. 21, 2010 which designated the U.S. and which claims priority to U.S. Provisional App. Ser. No. 61/289,155 filed Dec. 22, 2009. The noted applications are incorporated herein by reference.

STATEMENT REGARDING FEDERALLY SPONSORED RESEARCH OR DEVELOPMENT

Not applicable.

FIELD OF THE INVENTION

The present invention described herein generally relates to an etheramine mixture containing a monoether diamine, methods for its production, and its use as a curing agent or as a raw material in the synthesis of polymers.

BACKGROUND OF THE INVENTION

Polyetheramines are used widely used as curing agents for epoxy resins or as raw materials in the synthesis of polyamides or polyureas. Such polyetheramines are generally produced by the reaction of an alkylene oxide with an alcohol to form a polyoxyalkylene polyol and then subsequent conversion of the hydroxyl groups to amine groups by reductive amination.

For example, U.S. Pat. No. 3,654,370 describes a process in which a polyoxyalkylene polyol is treated with ammonia and hydrogen in the presence of a nickel oxide, copper oxide and chromium oxide catalyst to form a mixture of polyetheramines. U.S. Pat. No. 4,766,245 further describes a process in which high molecular weight polyoxyalkylene amines are produced by contacting high molecular weight polyoxyalkylene polyols with ammonia in the presence of hydrogen and a Raney nickel/aluminum catalyst. Additionally, U.S. Pat. No. 4,769,438 describes a process in which a propoxylated 1,4-butanediol is first aminated using a Raney nickel catalyst and then subsequently converted to an adduct by a reaction with a small amount of an epoxy resin. Finally, U.S. Pat. No. 7,550,550 describes a process for producing hindered polyetherdiamines and polyethertriamines by reductive animation of a variety of polyoxyalkylene polyols.

One drawback to polyetheramines produced by known processes is that they are formed from polyols having polyether groups in the polyol backbone. When used as a curing agent for epoxy resins, these polyether groups provide good flexibility in the cured resins, but also cause a significant reduction in their thermal properties. Attempts to reduce the amount of polyether groups in the polyol backbone by utilizing diols such as diethylene glycol and dipropylene glycol have proven unsuccessful, since these materials tend to undergo unwanted intramolecular side reactions during reductive amination to form large amounts of secondary amines, such as morpholine and 3,5-dimethyl morpholine, and only minor amounts of bis(aminoethyl)ether and bis(aminopropyl)ether.

Another drawback to current curing agents is the high temperatures typically required to cure these systems. For example, conventional hardener systems with cycloaliphatic diamines such as isophorone diamine, typically required 70° C. to 80° C. to cure. Heating a large mold from ambient temperature to 70° C. to 80° C. may take 3-4 hours, resulting in a slower manufacturing time.

Thus, needs exist for new amine curing agents that provide good flexibility and good thermal properties in the cured resin, as well as easily implemented processes for their production. Also, needs exist for new curing agents that have improved cure performance, such as allowing for curing at lower temperatures or for shorter periods of time.

SUMMARY OF THE INVENTION

The present disclosure relates to an etheramine mixture containing a monoether amine of formula:

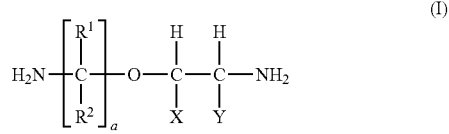

where $R^1$ and $R^2$ are identical or different and are each, independently of one another, hydrogen or a linear or branched $C_1$-$C_5$ alkyl group which may be optionally substituted by one or more $NH_2$ groups, a is an integer from 3 to 6, and X and Y are identical or different and are each, independently of one another, hydrogen, a linear or branched $C_1$-$C_5$ alkyl group, a linear or branched $C_2$-$C_5$ alkenyl group, or a substituted or unsubstituted $C_6$-$C_{12}$ aryl group.

The etheramine mixture containing the monoether amine of formula (I) may be produced by contacting an initiator with an alkylene oxide to form a precursor polyol and reductively aminating the hydroxyl groups on the precursor polyol to form the etheramine mixture.

Once produced, the etheramine mixture may be used in a variety of applications, such as a curing agent for epoxy resins, or as a reactant in the production of polymers. Thus, the etheramine mixture may be contacted with an epoxy resin under conditions suitable to cause the epoxy resin to cure or reacted with an organic polyisocyanate to form polyurea.

DETAILED DESCRIPTION OF THE INVENTION

Various embodiments of the present disclosure generally relate to an etheramine mixture containing a monoether amine of formula:

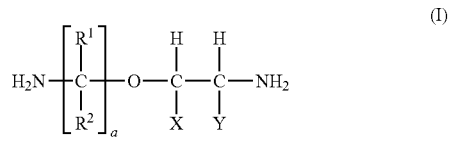

wherein $R^1$ and $R^2$ are identical or different and are each, independently of one another, hydrogen or a linear or branched $C_1$-$C_5$ alkyl group which may be optionally substituted by one or more $NH_2$ groups, a is an integer from 3 to 6, and X and Y are identical or different and are each, independently of one another, hydrogen, a linear or branched $C_1$-$C_5$ alkyl group, a linear or branched $C_2$-$C_5$ alkenyl group, or a substituted or unsubstituted $C_6$-$C_{12}$ aryl group. It has been surprisingly found that when the etheramine mixture of the present invention is used as a curing agent, it provides not only a cured product which exhibits good flexibility and elongation properties but also one having significantly improved thermal stability, in this case meaning an increased glass transition temperature. Such improved thermal stability is not possible with state of the art polyetheramine curing agents used alone.

In embodiments of the present invention, the curing agents disclosed may show improved cure performance. Such improved cure performance may include greater glass transition temperature build and strength development in castings baked at lower temperatures or for shorter periods of time than currently known curing agents. Such improved cure performance would result in a lower energy cost of production and/or a higher manufacturing rate.

The present disclosure further provides a process for preparing the etheramine mixture containing the monoether amine of formula (I) by: (i) charging an initiator to an alkoxylation reaction zone; (ii) contacting the initiator with an alkylene oxide in the alkoxylation reaction zone to provide a precursor polyol; and (iii) charging the precursor polyol to a reductive amination zone and catalytically reductively aminating the precursor polyol in the presence of a reductive amination catalyst, hydrogen and ammonia to form the etheramine mixture. The process of the present invention unexpectedly produces high yields of the monoether amine of formula (I) while minimizing the amounts of other polyetheramines, such as diether- and polyetheramines which are formed. Moreover, the amount of unwanted side reaction products produced during reductive amination, such as morpholine and substituted-morpholine, are also significantly reduced by the process of the present invention.

In still another embodiment, the present disclosure generally provides a process for producing a cured epoxy resin system by: (i) providing an etheramine mixture according to the present invention; (ii) providing an epoxy resin; (iii) contacting the etheramine mixture and the epoxy resin to form an epoxy resin system; and (iv) curing the epoxy resin system.

In still yet another embodiment, the present disclosure generally provides a process for producing a polyurea by reacting the etheramine mixture according to the present invention with an organic polyisocyanate.

According to one embodiment, the etheramine mixture contains at least 10% by weight, based on the total weight of the etheramine mixture, of the monoether amine of formula:

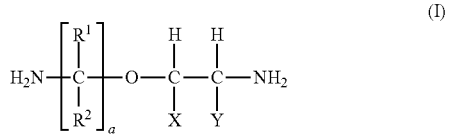

(I)

wherein $R^1$ and $R^2$ are identical or different and are each, independently of one another, hydrogen or a linear or branched $C_1$-$C_5$ alkyl group which may be optionally substituted by one or more $NH_2$ groups, a is an integer from 3 to 6, and X and Y are identical or different and are each, independently of one another, hydrogen, a linear or branched $C_1$-$C_5$ alkyl group, a linear or branched $C_2$-$C_5$ alkenyl group, or a substituted or unsubstituted $C_6$-$C_{12}$ aryl group. In one embodiment, a is 3. In another embodiment, $R^1$ and $R^2$ are independently selected from hydrogen and a linear or branched $C_1$-$C_3$ alkyl group. In still another embodiment, $R^1$ and $R^2$ are independently selected from hydrogen and $CH_3$. In yet another embodiment, X and Y are independently selected from hydrogen, $CH_3$, and $C_2H_5$.

According to some embodiments, the etheramine mixture contains at least about 20% by weight, preferably at least about 30% by weight, and more preferably at least about 40% by weight, based on the total weight of the etheramine mixture, of the monoether amine of formula (I). In other embodiments, the etheramine mixture contains from about 10% by weight to about 70% by weight, preferably from about 20% by weight to about 60% by weight, and more preferably from about 30% by weight to about 50% by weight, based on the total weight of the etheramine mixture, of the monoether amine of formula (I).

The overall process for producing the etheramine mixture of the present disclosure, which utilizes an initiator as the starting raw material, can be applied as a batch process or continuous process. In the first step, the initiator is charged to the alkoxylation reaction zone. The initiator may be any oxyalkylation susceptible polyhydric alcohol containing 2 to 4 hydroxyl groups. Examples of the initiator include: a diol such a 1,3-diol including 1,3-propandiol, 1,3-butanediol, neopentyl glycol, 2-methyl-1,3-propanediol and 2,2,4-trimethyl-1,3-pentanediol, hexylenediol; a triol, such as trimethylolpropane and triethylolpropane; and a tetrol such as pentraerythritol.

After charging, the initiator is then contacted with an alkylene oxide in the alkoxylation reaction zone for a period of time sufficient to provide a precursor polyol. The alkylene oxide may be an alkylene oxide having the formula:

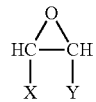

wherein X and Y are identical or different and are each, independently of one another, hydrogen, a linear or branched $C_1$-$C_5$ alkyl group, a linear or branched $C_2$-$C_5$ alkenyl group, or a substituted or unsubstituted $C_6$-$C_{12}$ aryl group. Preferably, the alkylene oxide is ethylene oxide, propylene oxide, butylene oxide (such as isobutylene oxide, 1,2-butylene oxide, and 2,3-butylene oxide), pentylene oxide, styrene oxide or a combination thereof. The amount of alkylene oxide which is contacted with the initiator may range from about 1.2-1.8 moles, preferably from about 1.4-1.6 moles, of alkylene oxide per mole of initiator. The period of time the initiator is contacted with the alkylene oxide is a period of time sufficient to form the precursor polyol and in some embodiments may range from about 0.5 hours to about 24 hours.

In one embodiment, the alkoxylation reaction zone is a closed reaction vessel and alkoxylation is carried out under elevated temperature and pressure and in the presence of a base catalyst. Thus, alkoxylation may be conducted at a temperature ranging from about 50° C. to about 150° C. and a pressure ranging from about 40 psi to about 100 psi. The base catalyst may be any alkaline compound customarily used for base-catalyzed reactions, for example, an alkali metal hydroxide such as sodium hydroxide, lithium hydroxide, potassium hydroxide, or cesium hydroxide, or a tertiary amine, such as dimethyl cyclohexylamine or 1,1,3,3-tetramethylguanidine. After alkoxylation, the resulting mixture may be vacuum stripped to remove any unnecessary components, such as excess unreacted alkylene oxide, water and/or base catalyst, while leaving the resulting precursor polyol.

The precursor polyol may then be used as a feedstock for the reductive amination step. Because the addition during alkoxylation is random, the precursor polyol formed in the alkoxylation reaction zone will not be a pure compound, but rather will be a mixture of monoether and polyether polyols. The proportion of these polyols can be varied considerably and driven to formation of monoether polyols by adjustment of the ratio of the alkylene oxide to the initiator in the alkoxylation reaction zone. Accordingly, in some embodiments, the precursor polyol will contain at least 10% by weight, preferably at least 20% by weight, more preferably at least about 30% by weight, and even more preferably at least about 40% by weight, based on the total weight of the precursor polyol, of a monoether polyol. In some embodiments, the precursor polyol will contain from about 10% by weight to about 70% by weight, preferably from about 20% by weight to about 60% by weight, and more preferably from about 30% by weight to about 50% by weight, based on the total weight of the precursor polyol, of a monoether polyol.

In some embodiments, prior to reductive amination, the precursor polyol may be neutralized with any suitable acid or chemical adsorbent, such as for example, oxalic acid or magnesium silicate, and filtered for the removal of insoluble materials. The precursor polyol is then charged to a reductive amination zone where it is brought into contact with a reductive amination catalyst, sometimes referred to as a hydrogenation-dehydrogenation catalyst, and reductively aminated in the presence of ammonia and hydrogen under reductive amination conditions. Reductive amination conditions may include, for example, a temperature within the range of about 150° C. to about 275° C. and a pressure within the range of about 500 to about 5000 psi with temperatures within the range of about 180° C. to about 220° C. and pressures within the range of about 1500 to about 2500 psi being preferred.

Any suitable hydrogenation catalyst may be used, such as those described in U.S. Pat. No. 3,654,370, the contents of which are incorporated herein by reference. In some embodiments, the hydrogenation catalyst may comprise one or more of the metals of group VIIIB of the Periodic Table, such as iron, cobalt, nickel, ruthenium, rhodium, palladium, platinum, mixed with one or more metals of group VIB of the Periodic Table such as chromium, molybdenum or tungsten. A promoter from group IB of the Periodic Table, such as copper, may also be included. As an example, a catalyst may be used comprising from about 60 mole percent to about 85 mole percent of nickel, about 14 mole percent to about 37 mole percent of copper and about 1 mole percent to about 5 mole percent of chromium (as chromia), such as a catalyst of the type disclosed in U.S. Pat. No. 3,152,998. As another example, a catalyst of the type disclosed in U.S. Pat. No. 4,014,933 may be used containing from about 70% by weight to about 95% by weight of a mixture of cobalt and nickel and from about 5% by weight to about 30% by weight of iron. As another example, a catalyst of the type disclosed in U.S. Pat. No. 4,152,353 may be used, comprising nickel, copper and a third component which may be iron, zinc, zirconium or a mixture thereof, for example, a catalyst containing from about 20% by weight to about 49% by weight of nickel, about 36% by weight to about 79% by weight of copper and about 1% by weight to about 15% by weight of iron, zinc, zirconium or a mixture thereof. As still another example, a catalyst of the type described in U.S. Pat. No. 4,766,245 may be used comprising about 60% by weight to about 75% by weight of nickel and about 25% by weight to about 40% by weight of aluminum.

The reductive amination is preferably conducted on a continuous basis with the precursor polyol, ammonia and hydrogen being continuously charged to a reactor containing a fixed bed of reductive amination catalyst and with the reaction product being continually withdrawn.

The reaction product is suitably depressured so as to recover excess hydrogen and ammonia for recycle and is then fractionated to remove byproduct water of reaction and to provide the desired etheramine mixture.

In conducting the reductive amination, the reductive amination conditions to be utilized may suitably include the use of from about 4 moles to about 150 moles of ammonia per hydroxyl equivalent of precursor polyol feedstock. Hydrogen is preferably used in an amount ranging from about 0.5 mole equivalents to about 10 mole equivalents of hydrogen per hydroxyl equivalent of precursor polyol feedstock. The contact times within the reaction zone, when the reaction is conducted on a batch basis, may suitably be within the range of from about 0.1 hours to about 6 hours and more preferably from about 0.15 hours to about 2 hours.

When the reaction is conducted on a continuous basis using catalyst pellets, reaction times may suitably be from about 0.1 grams to about 2 grams of feedstock per hour per cubic centimeter of catalyst and, more preferably, from about 0.3 grams to about 1.6 grams of feedstock per hour per cubic centimeter of catalyst.

Also, the reductive amination may be conducted in the presence of about 1 mole to about 200 moles of ammonia per mole of precursor polyol and more preferably, from about 4 moles to about 130 moles of ammonia per mole of precursor polyol. From about 0.1 moles to about 50 moles of hydrogen per mole of precursor polyol may be employed and, more preferably, from about 1 mole to about 25 moles of hydrogen per mole of precursor polyol.

Due to its favorable properties, the etheramine mixture according to the invention may be used as a constituent in a formulation which finds use in a wide variety of industrial applications, for example for the production of moldings (casting resins), fibre-reinforced composites, such as wind turbine generator blades, for tool manufacture or for the production of coatings and/or intermediate coatings on a wide variety of substrates, for example on substrates of an organic or inorganic nature, such as wood, wood fibers (wood sealing), textiles of natural or synthetic origin, plastics, glass, ceramics, building materials, such as concrete, fiberboard, and artificial stone, on metal, such as iron, aluminum, copper and the like. In addition, the etheramine mixture according to the present invention can be employed as a constituent of an adhesive, cement, laminating resin, synthetic resin cement, paint or coating. The formulation can be prepared anytime prior to or during use by contacting the constituents, for example by mixing, and it can also be applied to any type of surface(s), for example, by brushing, spraying, dipping coating, extruding, printing, electrostatically, and the like, and then subsequently cured to form a cured material.

According to one preferred embodiment, the etheramine mixture of the present invention containing the monoether amine of formula (I) is contacted with an epoxy resin to form an epoxy resin formulation. The epoxy resin formulation may then be subjected to conditions sufficient to cause the epoxy resin formulation to cure.

The epoxy resin may be any one or mixture of reactive epoxy resin(s) having a 1,2-epoxy equivalency (functionality), on the average, of at least 1 epoxide groups per molecule, preferably at least 1.3 epoxide groups per molecule, and more preferably at least 1.6 epoxide groups per molecule, and even more preferably with epoxy resins having a functionality of at least 2 epoxy groups per molecule such that the mixture will polymerize to form a useful material with the amine of the current invention or its blend with other amine hardeners. In another embodiment, the epoxy resin has a functionality on the average ranging from at least 1.3 epoxide groups per molecule to about 8 epoxide groups per molecule, preferably from at least about 1.6 epoxide groups per molecule to about 5 epoxide groups per molecule. The epoxy resin can be saturated or unsaturated, linear or branched, aliphatic, cycloaliphatic, aromatic or heterocyclic, and may bear substituents such as bromine or fluorine. It may be monomeric or polymeric, liquid or solid, but is preferably liquid or a low melting solid at room temperature.

According to one embodiment, the epoxy resin is a polyglycidyl epoxy compound, such as a polyglycidyl ether, poly(β-methylglycidyl)ether, polyglycidyl ester or poly(β-methylglycidyl)ester. The synthesis and examples of polyglycidyl ethers, poly(β-methylglycidyl)ethers, polyglycidyl esters and poly(β-methylglycidyl)esters are disclosed in U.S. Pat. No. 5,972,563, which is incorporated herein by reference. For example, ethers may be obtained by reacting a compound having at least one free alcoholic hydroxyl group and/or phenolic hydroxyl group with a suitably substituted epichlorohydrin under alkaline conditions or in the presence of an acidic catalyst followed by alkali treatment. The alcohols may be, for example, acyclic alcohols, such as ethylene glycol, diethylene glycol and higher poly(oxyethylene)glycols, propane-1,2-diol, or poly(oxypropylene)glycols, propane-1,3-diol, butane-1,4-diol, poly(oxytetramethylene)glycols, pentane-1,5-diol, hexane-1,6-diol, hexane-2,4,6-triol, glycerol, 1,1,1-trimethylolpropane, bistrimethylolpropane, pentaerythritol and sorbitol. Suitable glycidyl ethers may also be obtained, however, from cycloaliphatic alcohols, such as 1,3- or 1,4-dihydroxycyclohexane, bis(4-hydroxycyclo-hexyl)methane, 2,2-bis(4-hydroxycyclohexyl)propane or 1,1-bis(hydroxymethyl)cyclohex-3-ene, or they may possess aromatic rings, such as N,N-bis(2-hydroxyethyl)aniline or p,p'-bis(2-hydroxyethylamino)diphenylmethane.

Representative examples of polyglycidyl ethers or poly(β-methylglycidyl)ethers include those based on monocyclic phenols, for example, on resorcinol or hydroquinone, on polycyclic phenols, for example, on bis(4-hydroxyphenyl)methane(Bisphenol F), 2,2-bis(4-hydroxyphenyl)propane (Bisphenol A), bis(4-hydroxyphenyl)S (Bisphenol S), alkoxylated Bisphenol A, F or S, triol extended Bisphenol A, F or S and brominated Bisphenols A, F or S, hydrogenated Bisphenol A, F or S, glycidyl ethers of phenols and phenols with pendant groups or chains, on condensation products, obtained under acidic conditions, of phenols or cresols with formaldehyde, such as phenol novolaks and cresol novolaks, or on siloxane diglycidyls.

Polyglycidyl esters and poly(β-methylglycidyl)esters may be produced by reacting epichlorohydrin or glycerol dichlorohydrin or β-methylepichlorohydrin with a polycarboxylic acid compound. The reaction is expediently carried out in the presence of bases. The polycarboxylic acid compounds may be, for example, glutaric acid, adipic acid, pimelic acid, suberic acid, azelaic acid, sebacic acid or dimerized or trimerized linoleic acid. Likewise, however, it is also possible to employ cycloaliphatic polycarboxylic acids, for example tetrahydrophthalic acid, 4-methyltetrahydrophthalic acid, hexahydrophthalic acid or 4-methylhexahydrophthalic acid. It is also possible to use aromatic polycarboxylic acids such as, for example, phthalic acid, isophthalic acid, trimellitic acid or pyromellitic acid, or else carboxyl-terminated adducts, for example of trimellitic acid and polyols, for example glycerol or 2,2-bis(4-hydroxycyclohexyl)propane, can be used.

In another embodiment, the epoxy resin is a non-glycidyl epoxy compound. Non-glycidyl epoxy compounds may be linear, branched, or cyclic in structure. For example, there may be included one or more epoxide compounds in which the epoxide groups form part of an alicyclic or heterocyclic ring system. Others include an epoxy-containing compound with at least one epoxycyclohexyl group that is bonded directly or indirectly to a group containing at least one silicon atom. Examples are disclosed in U.S. Pat. No. 5,639,413, which is incorporated herein by reference. Still others include epoxides which contain one or more cyclohexene oxide groups and epoxides which contain one or more cyclopentene oxide groups. Particularly suitable non-glycidyl epoxy compound's include the following difunctional non-glycidyl epoxide compounds in which the epoxide groups form part of an alicyclic or heterocyclic ring system: bis(2,3-epoxycyclopentyl)ether, 1,2-bis(2,3-epoxycyclopentyloxy)ethane, 3,4-epoxycyclohexyl-methyl 3,4-epoxycyclohexanecarboxylate, 3,4-epoxy-6-methyl-cyclohexylmethyl 3,4-epoxy-6-methyl-cyclohexanecarboxylate, di(3,4-epoxycyclohexylmethyl)hexanedioate, di(3,4-epoxy-6-methylcyclohexylmethyl)hexanedioate, ethylenebis(3,4-epoxycyclohexanecarboxylate), ethanediol di(3,4-epoxycyclohexylmethyl)ether, vinylcyclohexene dioxide, dicyclopentadiene diepoxide or 2-(3,4-epoxycyclohexyl-5,5-spiro-3,4-epoxy)cyclohexane-1,3-dioxane, and 2,2'-bis-(3,4-epoxy-cyclohexyl)-propane.

In another embodiment, the epoxy resin is an epoxy novolac compound obtained by the reaction of, preferably in the presence of a basic catalyst such as sodium or potassium hydroxide, an epihalohydrin, such as epichlorohydrin, with a resinous condensate of an aldehyde, such as formaldehyde and either a monohydric phenol or polyhydric phenol.

In other embodiments, the epoxy resin is a poly(N-glycidyl) compound or poly(S-glycidyl) compound. Poly(N-glycidyl) compounds are obtainable, for example, by dehydrochlorination of the reaction products of epichlorohydrin with amines containing at least two amine hydrogen atoms. These amines may be, for example, n-butylamine, aniline, toluidine, m-xylylenediamine, bis(4-aminophenyl)methane or bis(4-methylaminophenyl)methane. Other examples of poly(N-glycidyl) compounds include N,N'-diglycidyl derivatives of cycloalkyleneureas, such as ethyleneurea or 1,3-propyleneurea, and N,N'-diglycidyl derivatives of hydantoins, such as of 5,5-dimethylhydantoin. Examples of poly(S-glycidyl) compounds are di-S-glycidyl derivatives derived from dithiols, for example ethane-1,2-dithiol or bis(4-mercaptomethylphenyl)ether.

It is also possible to employ epoxy-containing compounds in which the 1,2-epoxide groups are attached to different heteroatoms or functional groups. Examples of these compounds include the N,N,O-triglycidyl derivative of 4-aminophenol, the glycidyl ether/glycidyl ester of salicylic acid, N-glycidyl-N'-(2-glycidyloxypropyl)-5,5-dimethylhydantoin or 2-glycidyloxy-1,3-bis(5,5-dimethyl-1-glycidylhydantoin-3-yl)propane.

Other epoxide derivatives may be employed, such as vinyl cyclohexene dioxide, limonene dioxide, limonene monoxide, vinyl cyclohexene monoxide, 3,4-epoxycyclohexlmethyl acrylate, 3,4-epoxy-6-methyl cyclohexylmethyl 9,10-epoxystearate, and 1,2-bis(2,3-epoxy-2-methylpropoxy)ethane. Also conceivable is the use of oxetanes or liquid pre-reacted adducts of epoxy-containing compounds, such as those mentioned above, with hardeners for the epoxy resins.

The epoxy resin formulation may further contain customary additives and auxiliaries such as stabilizers, modifiers, antifoaming agents, toughening agents, accelerators, co-curing agents, leveling agents, thickening agents, flame retardants, antioxidants, pigments, dyes, fillers, and combinations thereof. For example, an accelerator such as guanidine or a derivative thereof may be used in the epoxy resin formulation. Examples of guanidine derivatives include without limitation, an alkylguanidine such as dimethylguanidine or tetramethyl guanidine, or a guanidinium salt derived from any of these. Examples of guanidinium salts include without limitation, guanidine carbonates, guanidine acetates, and guanidine nitrates. One skilled in the art with the benefit of this disclosure will recognize appropriate additives and auxiliaries for use in embodiments of the present invention.

In embodiments of the present invention, the etheramine mixtures may not require the use of co-curing agent, such as cycloaliphatic diamines such as isophorone diamine. In these embodiments, fewer materials would be needed to manufacture the epoxy resin as well as less energy needed to reach the lower cure temperature.

Once formulated, the epoxy resin formulation may be applied to one or more surfaces, for example, brushing, spraying, dipping, etc., and subjected to conditions suitable to cause the epoxy resin system to cure. In one embodiment, the epoxy resin formulation is cured at ambient conditions. In another embodiment, the epoxy resin formulation is cured at an elevated temperature such as, at a temperature within the range from about 40° C. to about 220° C. In some embodiments of the present invention, a lower cure temperature and/or lower cure time may be needed to reach desired cure properties, such as glass transition temperatures, than is typically required in current epoxy resin systems. Achieving improved cure property development at lower curing (such as baking) temperatures and/or shorter curing times means a potential savings in energy costs and a possible reduction in manufacturing process time (increased productivity). In embodiments of the present invention, the temperature used in curing may be about, or less than, 40° C., 45° C., 50° C., 55° C., 60° C. and 65° C. In embodiments of the present invention, the cure time may be from about 2 hours (hrs) to about 6 hrs, including the intervals of about 2.5 hrs, 3 hrs, 3.5 hrs, 4 hrs, 4.5 hrs, 5 hrs and 5.5 hrs. In an embodiment of the present invention, the epoxy resin system is cured from about 3 to about 6 hours at about 55° C. One skilled in the art will recognize, with the benefit of this disclosure, how to reach desired cure properties using lower temperatures and/or lower cure times.

In still another embodiment, the etheramine mixture of the present disclosure is reacted with an organic polyisocyanate to form a polyurea. The organic polyisocyanate includes standard isocyanate compounds and compositions known to those skilled in the art. Preferred examples include MDI-based quasi prepolymers such as those commercially available as RUBINATE® 9480, RUBINATE® 9484, and RUBINATE® 9495 brand products which are all available from Huntsman International, LLC. Liquefied MDI such as MONDUR® ML isocyanate, available from Bayer MaterialScience, may also be used as all or part of the isocyanate.

Other organic polyisocyanates which can be employed include those generally known to one skilled in the art. Thus, for instance, they can include aliphatic isocyanates of the type described in U.S. Pat. No. 4,748,192. Accordingly, they are typically aliphatic diisocyanates and, more particularly, are the trimerized or the biuretic form of an aliphatic diisocyanate, such as hexamethylene diisocyanate, or the bifunctional monomer of the tetraalkyl xylene diisocyanate, such as the tetramethyl xylene diisocyanate. Another example of an aliphatic isocyanate is cyclohexane diisocyanate. Other useful aliphatic isocyanates are described in U.S. Pat. No. 4,705,814 which is fully incorporated herein by reference. They include aliphatic diisocyanates, for example, alkylene diisocyanates with 4 to 12 carbon atoms in the alkylene radical, such as 1,12-dodecane diisocyanate and 1,4-tetramethylene diisocyanate. Also described are cycloaliphatic diisocyanates, such as 1,3 and 1,4-cyclohexane diisocyanate as well as any desired mixture of these isomers, 1-isocyanato-3,3,5-trimethyl-5-isocyanato methylcyclohexane(isophorone diisocyanate); 4,4'-,2,2'- and 2,4'-dicyclohexylmethane diisocyanate as well as the corresponding isomer mixtures, and the like.

A wide variety of aromatic polyisocyanates may also be used to form the polyurea of the present disclosure. Typical aromatic polyisocyanates include p-phenylene diisocyanate, polymethylene polyphenylisocyanate, 2,6-toluene diisocyanate, dianisidine diisocyanate, bitolylene diisocyanate, naphthalene-1,4-diisocyanate, bis(4-isocyanatophenyl)methane, bis(3-methyl-3-iso-cyanatophenyl)methane, bis(3-methyl-4-isocyanatophenyl)methane, and 4,4'-diphenylpropane diisocyanate. Other aromatic polyisocyanates which may be used are methylene-bridged polyphenyl polyisocyanate mixtures which have a functionality of from about 2 to about 4. These latter isocyanate compounds are generally produced by the phosgenation of corresponding methylene bridged polyphenyl polyamines, which are conventionally produced by the reaction of formaldehyde and primary aromatic amines, such as aniline, in the presence of hydrochloric acid and/or other acidic catalysts. Known processes for preparing polyamines and corresponding methylene-bridged polyphenyl polyisocyanates therefrom are described in the literature and in many patents, for example, U.S. Pat. Nos. 2,683,730; 2,950,263; 3,012,008; 3,344,162 and 3,362,979, all of which are fully incorporated herein by reference. Usually, methylene-bridged polyphenyl polyisocyanate mixtures contain about 20 to about 100 weight percent methylene diphenyl diisocyanate isomers, with the remainder being polymethylene polyphenyl diisocyanates having higher functionalities and higher molecular weights. Typical of these are polyphenyl polyisocyanate mixtures containing about 20 to about 100 weight percent diphenyl diisocyanate isomers, of which about 20 to about 95 weight percent thereof is the 4,4'-isomer with the remainder being polymethylene polyphenyl polyisocyanates of higher molecular weight and functionality that have an average functionality of from about 2.1 to about 3.5. These isocyanate mixtures are known, commercially available materials and can be prepared by the process described in U.S. Pat. No. 3,362,979. A preferred aromatic polyisocyanate is methylene bis(4-phenylisocyanate) or "MDI". Pure MDI, quasi-prepolymers of MDI, modified pure MDI, etc. are useful to prepare a polyurea according to the invention. Since pure MDI is a solid and, thus, often inconvenient to use, liquid products based on MDI or methylene bis(4-phenylisocyanate) are used herein. U.S. Pat. No. 3,394,164, incorporated herein by reference, describes a liquid MI product. More generally, uretonimine modified pure MDI is included also. This product is made by heating pure distilled MDI in the presence of a catalyst. The liquid product is a mixture of pure MDI and modified MDI. The term organic polyisocyanate also includes quasi-prepolymers of isocyanates or polyisocyanates with active hydrogen containing materials.

EXAMPLES

Example 1

To a dry, nitrogen-purged reactor were added 3000 grams of 99% 2,2-dimethyl-1,3-propanediol (or neopentyl glycol) and 90 grams of N, N-dimethyl cyclohexylamine (DMCHA). The reaction mixture was then heated under nitrogen to 125°-130° C. 320 grams of propylene oxide was initially added slowly to the reaction mixture. An additional 2000 grams of propylene oxide was then further added to the reaction mixture at a temperature of about 120° C. and the reaction mixture was digested down to constant pressure. The diol mixture was cooled to 100° C. and non-reacted propylene oxide was vented. The diol mixture was then stripped at 50 mm Hg for about one hour to remove any light reactants and water. The final diol mixture that was produced was a low-color, mobile liquid weighing 5250 grams having a hydroxyl number of 597.

The final diol mixture was then reductively aminated with ammonia in a 100 cc continuous tubular reactor using a solid catalyst as described in U.S. Pat. No. 3,654,370. The catalyst, in the form of ⅛ inch×⅛ inch tablets containing nickel, copper and chromium, was charged to the 100 cc continuous tubular reactor. The final diol mixture and ammonia were pumped separately and mixed in-line with hydrogen and then fed through the catalyst bed for a period of about 33 hours. The final diol mixture and ammonia were kept at an approximate 1:1 weight feed ratio, while the ammonia to hydrogen ratio was kept at about a 20:1 weight feed ratio. The reactor temperature was maintained at 190°-220° C. for the entire reductive amination step. The final product was collected, vented of excess ammonia and stripped in a rotary evaporator to remove light amines and water. A total of 4959 grams of a low-color etheramine mixture was recovered having an average molecular weight of about 200 and an amine concentration of about 98.1%. The etheramine mixture contained about 50% by weight of monoether diamine, about 33% by weight of diether diamine and only about 8% by weight of 3,6,6-trimethyl homomorpholine, all based on the total weight of the etheramine mixture, as determined by gas chromatography and distillation.

Example 2

Example 1 was repeated except that 2000 grams of 99% 1,3-butylene glycol and 50 grams of DMCHA were added to the nitrogen-purged kettle and heated to about 100° C. and then 1930 grams of propylene oxide slowly added to the reaction mixture over a one-hour time period. The final diol mixture that was obtained was a light yellow, mobile liquid, weighing 1850 grams, a hydroxyl number of about 617 and a water content of 0.035%.

The final diol mixture was then reductively animated in the presence of ammonia and hydrogen as in Example 1 for a period of about 20 hours. A total of about 1155 grams of a light yellow etheramine mixture was recovered having an amine concentration of about 94.2%. The etheramine mixture contained about 33% by weight of monoether diamine and about 44% by weight of diether diamine, based on the total weight of the etheramine mixture, as determined by gas chromatography.

Example 3

An epoxy resin formulation containing bisphenol A resin (produced from bisphenol A and epichlorohydrin) and bisphenol F resin (produced from bisphenol F and epichlorohydrin) having an epoxy equivalent weight of 172 was cured using the etheramine mixtures of Examples 1 and 2 as well as by a commercially available curing agent (JEFFAMINE® D-230 amine) containing no monoether amine components and, bis-aminoethyl ether (BAEE), a pure monoether diamine. The epoxy resin blend and amine curing agent were mixed in the amounts listed below in Table 1 to form epoxy formulations A-D and then cured at 80° C. for six hours. The glass transition temperature ($T_g$) of the cured material was then measured using a differential scanning calorimeter (DSC) and choosing the temperature at the inflection point of the heat capacity change as the $T_g$. The results are presented below in Table 1:

TABLE 1

|  | Formulation A | Formulation B | Formulation C | Formulation D |
|---|---|---|---|---|
| Epoxy Resin Blend | 100 pbw | 100 pbw | 100 pbw | 100 pbw |
| Example 1 | 31 pbw |  |  |  |
| Example 2 |  | 30 pbw |  |  |
| JEFFAMINE ® D-230 amine |  |  | 35.5 pbw |  |
| BAEE |  |  |  | 17 pbw |
| $T_g$ after 6 hours at 80° C. | 78.5° C. | 73° C. | 65° C. | 82° C. |

The $T_g$ obtained for cured Formulations A and B compared favorably with that obtained for cured Formulation D, which was cured using pure monoether diamine BAEE thus demonstrating the etheramine mixtures of the present invention produce cured materials exhibiting excellent thermal properties. However, a significant reduction in the thermal properties was observed for cured Formulation C, which was cured using a non-monoether amine containing amine curing agent.

The following tables 2 and 3 compare two commercial formulations (Commercial A and Commercial B) to formulations of the present invention (Formulations E and F). Formulations E and F include the etheramine mixture prepared in Example 1. In the tables below, EEW stands for epoxy equivalent weight expressed in gram/equivalent. The commercial curing agent is JEFFAMINE®D-230 amine. Co-curing agent #1 is a cycloaliphatic diamine(isophorone diamine). Co-curing agent #2 is also a cycloaliphatic amine(cyclohexanedimethanamine). The accelerator is N-Aminoethylpiperazine (AEP). DSC stands for differential scanning calorimetry, a technique that is used to determine the optimum amine to epoxy ratio, by measuring optimum Tg. The optimized ratio, or optimim phr (phr stands for weight part of the amine for 100 parts per weight of the epoxy resin) is the epoxy to amine ratio that gives the highest Tg.

Table 2 investigates the cure behavior in terms of Tg build and mechanical strength development of two formulations of the present invention compared to two commercial formulations, when baked at lower temperatures in the 50° C. to 60° C. range, and/or for a shorter period of time.

TABLE 2

|  | Commercial A | Commercial B | Formulation E | Formulation F |
|---|---|---|---|---|
| Part A: parts by weight (pbw) | | | | |
| Diluted Bis A/F epoxy resin (EEW 172) | 100 pbw | 100 pbw | 100 pbw | 100 pbw |
| Part B: weight % | | | | |
| Commercial curing agent | 70% | 65% | — | — |
| Co-curing agent #1 | 30% | 20% | 20% | — |
| Co-curing agent #2 | — | — | — | 30% |
| Accelerator | — | 15% | — | — |
| Example 1 | — | — | 80% | 70% |
| Optimum phr of Part B (DSC) | 34 | 33 | 29.5 | 29 |
| 1$^{st}$ heat inflection Tg by DSC, ° C. | | | | |
| Tg @ 6 hours (hrs) at 50° C. | 57.5 | 60 | 65 | 65.5 |
| Tg @ 6 hrs at 60° C. | 70 | 71 | 69 | 76 |
| Tg @ 1.5 hrs at 70° C. and Tg @ 6 hrs at 70° C. (in parenthesis) | 54 (77) | 66.5 (79) | 69 (82.5) | 76 (84) |

Table 2 shows that higher Tg's are reached at the lower baking temperatures for the formulations with the etheramine mixture of the present invention, compared to the two reference formulations Commercial A and Commercial B. The test results demonstrate a higher Tg development in the etheramine mixture of the present invention. This indicates that the etheramine mixture would develop green strength faster, also at a lower baking temperature. Improved property development at lower baking temperature and/or after shorter baking times would mean energy savings and reduction in manufacturing process time (increased productivity).

Table 2 also shows Tg data for castings cured for a shorter period of time (1.5 hour, at 70° C.). This data also indicates higher Tg build for Formulations E and F compared to the reference formulations Commercial A and B.

Table 3 gives the composition details and the tensile strength properties for Formulations E and F of the present invention compared with two commercial formulations. Listed is mechanical property data for castings cured for 3 hours at 70° C. Data following in parentheses is data for 6 hrs at 80° C. In this table strength measurements are in GigaPascal (GPa) and MegaPascal (MPa).

TABLE 3

|  | Commercial A | Commercial B | Formulation E | Formulation F |
|---|---|---|---|---|
| Part A: parts by weight (pbw) | | | | |
| Diluted Bis A/F epoxy resin (EEW 172) | 100 pbw | 100 pbw | 100 pbw | 100 pbw |
| Part B: weight % | | | | |
| Commercial curing agent | 70% | 65% | — | — |
| Co-curing Agent #1 | 30% | 20% | 20% | — |
| Co-curing Agent #2 | — | — | — | 30% |
| Accelerator | — | 15% | — | — |
| Example 1 | — | — | 80% | 70% |
| Optimum phr of Part B (DSC) | 34 | 33 | 29.5 | 29 |
| Tensile modulus, GPa (see last paragraph for values in parentheses) | 2.5 (3.1) | 3.1 (3.0) | 2.8 (3.2) | 3.2 (3.0) |
| Max. tensile strength, MPa | 37 (76.5) | 48 (78) | 40.3 (83.5) | 75 (81.7) |
| % Elongation at max strength | 2.6 (4.4) | 1.7 (4.5) | 2.3 (4.2) | 3.5 (4.8) |
| % Elongation at break | 11 (6.3) | 1.7 (6.0) | 3.4 (5.5) | 4.2 (6.7) |

Table 3 indicates a faster development of tensile strength for the formulations with the new etheramine mixture compared to the Commercial A formulation and similar development of tensile strength without the use of an accelerator compared to the Commercial B formulation. Faster development of tensile strength indicates faster green strength development and faster demolding which would mean a reduction in manufacturing process time and energy cost saving.

The above-disclosed subject matter is to be considered illustrative, and not restrictive, and the appended claims are intended to cover all such modifications, enhancements, and other embodiments, which fall within the true scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. An etheramine mixture comprising:
   at least 10% by weight, based on the total weight of the etheramine mixture, of a monoether amine of formula (I):

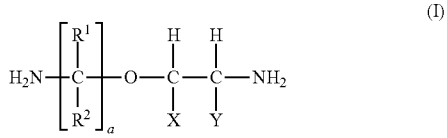 (I)

wherein $R^1$ and $R^2$ are identical or different and are each, independently of one another, hydrogen or a linear or branched $C_1$-$C_5$ alkyl group which may be optionally substituted by one or more $NH_2$ groups, a is an integer from 3 to 6, and X and Y are identical or different and are each, independently of one another, hydrogen, a linear or branched $C_1$-$C_5$ alkyl group, a linear or branched $C_2$-$C_5$ alkenyl group, or a substituted or unsubstituted $C_6$-$C_{12}$ aryl group, and
   wherein at least one of $R^1$ and $R^2$ is the linear or branched $C_1$-$C_5$ alkyl group which may be optionally substituted by one or more $NH_2$ groups; and
   at least one polyetheramine.

2. The etheramine mixture according to claim 1, wherein a is 3.

3. The etheramine mixture according to claim 2, wherein $R^1$ is hydrogen and $R^2$ is a linear or branched $C_1$-$C_3$ alkyl group.

4. The etheramine mixture according to claim 3, wherein $R^1$ is hydrogen and $R^2$ is $CH_3$.

5. The etheramine mixture according to claim 2, wherein X and Y are independently selected from hydrogen, $CH_3$, and $C_2H_5$.

6. The etheramine mixture according to claim 1, wherein the etheramine mixture contains at least about 30% by weight, based on the total weight of the etheramine mixture, of the monoether amine of formula (I).

7. The etheramine mixture according to claim 1, wherein the etheramine mixture contains from about 30% by weight to about 50% by weight, based on the total weight of the etheramine mixture, of the monoether amine of formula (I).

8. A process for preparing an etheramine mixture comprising:
   (i) charging an initiator to an alkoxylation reaction zone;
   (ii) contacting the initiator with an alkylene oxide in the alkoxylation reaction zone to provide a precursor polyol, wherein the alkoxylation reaction zone is maintained at a temperature from about 50° C. to about 150 ° C. and a pressure ranging from about 40 psi to about 100 psi; and
   (iii) charging the precursor polyol to a reductive amination zone and reductively aminating the precursor polyol in the presence of a reductive amination catalyst, hydrogen and ammonia to form the etheramine mixture,
   wherein the etheramine mixture contains at least 10% by weight, based on the total weight of the etheramine mixture, of a monoether amine of formula (I):

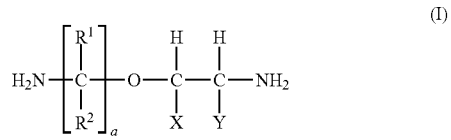 (I)

wherein $R^1$ and $R^2$ are identical or different and are each, independently of one another, hydrogen or a linear or branched $C_1$-$C_5$ alkyl group which may be optionally substituted by one or more $NH_2$ groups, a is an integer from 3 to 6, and X and Y are identical or different and are each, independently of one another, hydrogen, a linear or branched $C_1$-$C_5$ alkyl group, a linear or branched $C_2$-$C_5$ alkenyl group, or a substituted or unsubstituted $C_6$-$C_{12}$ aryl group,
   wherein at least one of $R^1$ $R^2$ is the linear or branched $C_1$-$C_5$ alkyl group which may optionally be substituted by one or more $NH_2$ groups; and
   wherein hydrogen is used in an amount ranging from about 0.5 mole equivalents To about 10 mole equivalents of hydrogen per hydroxyl equivalent of the precursor polyol.

9. The process according to claim 8 wherein the initiator is a 1,3-diol.

10. The process according to claim 8 wherein the initiator is selected from 1,3-butanediol, neopentyl glycol, 2-methyl-1,3-propanediol, 2,2,4-trimethyl-1,3-pentanediol, trimethylolpropane, triethylolpropane; and pentaerythritol.

11. The process according to claim 8 wherein the alkylene oxide is propylene oxide.

12. The process according to claim 8 wherein the alkylene oxide is butylene oxide.

13. The process according to claim 8 wherein the amount of alkylene oxide which is contacted with the initiator ranges from about 1.2-1.8 moles of alkylene oxide per mole of initiator.

14. The process according to claim 13 wherein the amount of alkylene oxide which is contacted with the initiator ranges from about 1.4-1.6 moles of alkylene oxide per mole of initiator.

15. A process for producing an epoxy resin system comprising:
   (i) providing an etheramine mixture of claim 1;
   (ii) providing an epoxy resin; and
   (iii) contacting the etheramine mixture and the epoxy resin to form an epoxy resin system.

16. A process for producing a cured epoxy resin system comprising:
   (i) providing an etheramine mixture of claim 1;
   (ii) providing an epoxy resin;
   (iii) contacting the etheramine mixture and the epoxy resin to form an epoxy resin system; and
   (iv) curing the epoxy resin system.

17. A process according to claim 16 wherein curing the epoxy resin system comprises curing the epoxy resin system from about 3 to about 6 hours at about 55° C.

18. A process for producing a polyurea comprising reacting the etheramine mixture of claim 1 with an organic polyisocyanate.

19. A polyurea produced by the process of claim 18.

20. An etheramine mixture produced by a process comprising the steps of:
   (i) charging an initiator to an alkoxylation reaction zone;
   (ii) contacting the initiator with an alkylene oxide in the alkoxylation reaction zone to provide a precursor polyol; and
   (iii) charging the precursor polyol to a reductive amination zone and reductively aminating the precursor polyol in the presence of a reductive amination catalyst, hydrogen and ammonia to form the etheramine mixture,
wherein the etheramine mixture contains;
   at least 10% by weight, based on the total weight of the etheramine mixture, of a monoether amine of formula (I):

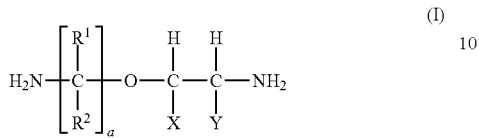

wherein $R^1$ and $R^2$ are identical or different and are each, independently of one another, hydrogen or a linear or branched $C_1$-$C_5$ alkyl group which may be optionally substituted by one or more $NH_2$ groups, a is an integer from 3 to 6, and X and Y are identical or different and are each, independently of one another, hydrogen, a linear or branched $C_1$-$C_5$ alkyl group, a linear or branched $C_2$-$C_5$ alkenyl group, or a substituted or unsubstituted $C_6$-$C_{12}$ aryl group, and
wherein at least one of $R^1$ and $R^2$ is the linear or branched $C_1$-$C_5$ alkyl group which may be optionally substituted by one or more $NH_2$ groups; and
at least one polyetheramine.

* * * * *